US005596196A

United States Patent [19]
Cooper et al.

[11] Patent Number: 5,596,196
[45] Date of Patent: Jan. 21, 1997

[54] OXYGENATE ANALYSIS AND CONTROL BY RAMAN SPECTROSCOPY

[75] Inventors: John B. Cooper, Virginia Beach; Kent L. Wise, Portsmouth, both of Va.; William T. Welch, Ashland, Ky.; Michael B. Sumner, Huntington, W. Va.

[73] Assignee: Ashland Inc., Ashland, Ky.

[21] Appl. No.: 449,326

[22] Filed: May 24, 1995

[51] Int. Cl.$^6$ ........................... G01J 3/44
[52] U.S. Cl. ........................ 250/339.12; 250/339.07; 250/339.08; 250/339.09; 356/301
[58] Field of Search ................ 356/301; 250/339.09, 250/339.08, 339.07, 339.12

[56] References Cited

U.S. PATENT DOCUMENTS

| | | | |
|---|---|---|---|
| 2,527,121 | 10/1950 | Dudenbostil, Jr. | 88/14 |
| 2,527,122 | 10/1950 | Heigel et al. | 88/14 |
| 3,371,574 | 3/1968 | Dwyer | 88/14 |
| 4,707,603 | 11/1987 | Miemelä et al. | 250/339 |
| 4,839,516 | 6/1989 | Freeman et al. | 250/255 |
| 4,963,745 | 10/1990 | Maggard | 250/343 |
| 4,994,671 | 2/1991 | Safinya et al. | 250/255 |
| 5,112,127 | 5/1992 | Carrabba et al. | 356/301 |
| 5,139,334 | 8/1992 | Clarke | 356/301 |
| 5,145,785 | 9/1992 | Maggard et al. | 436/8 |
| 5,190,882 | 3/1993 | Schulz et al. | 436/139 |
| 5,225,679 | 7/1993 | Clarke et al. | 250/343 |
| 5,243,546 | 9/1993 | Maggard | 364/571.02 |
| 5,262,644 | 11/1993 | Maguire | 250/339 |
| 5,266,800 | 11/1993 | Mullins | 250/256 |
| 5,348,645 | 9/1994 | Maggard et al. | 208/209 |
| 5,349,188 | 9/1994 | Maggard | 250/339 |
| 5,349,189 | 9/1994 | Maggard | 250/339.07 |
| 5,362,965 | 11/1994 | Maggard | 250/339.12 |
| 5,370,790 | 12/1994 | Maggard et al. | 208/142 |
| 5,412,465 | 5/1995 | Baylor et al. | 356/301 |

OTHER PUBLICATIONS

S. Michael Angel, Thomas M. Vess, and Michael L. Myrick, "Simultaneous Multi–point Fiber–optic Raman Sampling for Chemical Process Control Using Diode Lasers and a CCDDetector." *SPIE Chemical, Biochemical, and Environmental Fiber Sensors III*, vol. 1587 (1991) pp. 219–231.

M. B. Seasholtz, D. D. Archibald, A. Lorber, and B. R. Kowalksi, "Quantitative Analysis of Liquid Fuel Mixtures with the Use of Fourier Transform Near–IR Raman Spectroscopy." *Applied Spectroscopy*, vol 43, No. 6 (1989) pp. 1067–1072.

"Fiber Optic Raman System for On–Line Process Control of a Petroleum Pipeline" by M. L. Myrick and S. M. Angel and M. P. Gallagher; pp. 1–12 no date.

"U.S. Reformulated Gasoline Rule Complex, Confusing" by A. K. Rhodes; Oil and Gas Journal; Jan. 17, 1994; pp. 16–20.

"Natural Gas and Refined Products" by J. B. Hooper; Analytical Chemistry; vol. 65 No. 12; Jun. 15, 1993; pp. 189–192.

"A Comparison of Methods to Determine Benzene in Gasoline Boiling Range Material" by R. E. Pauls et al.; Journal of Chromatographic Science; vol. 30 Jan. 1992; pp. 32–39.

"Remote Near–IR Spectroscopy Over an Optical Fiber with a Modified FT Spectrometer" by D. D. Archibald et al.; Applied Spectroscopy; vol. 42, No. 3; 1988; pp. 468–472. no month.

"Quantitative Analysis of Liquid Fuel Mixtures with the Use of Fourier Transform Near–IR Raman Spectroscopy" by M. B. Seasholtz et al.; Applied Spectroscopy; vol. 43 No. 6, 1989; pp. 1067–1072 no month.

(List continued on next page.)

*Primary Examiner*—Constantine Hannaher
*Attorney, Agent, or Firm*—Richard C. Willson, Jr.; Richard D. Stone

[57] ABSTRACT

Oxygenated hydrocarbons can be predicted within ±0.2% wt or better, using Raman NIR spectroscopy and multivariate analysis, with optional fiberoptics multistreaming. The resulting signal can be used to control concentration of such compounds in product to desired levels.

39 Claims, 7 Drawing Sheets

OTHER PUBLICATIONS

"Determination of Gas Oil Cetane Number and Cetane Index Using Near–Infrared Fourier Transform Raman Spectroscopy" by K. P. J. Williams et al. *Anal. Chem.* 1990 62 pp. 2553–2556. no month.

"Fiber–Optic Sampling Combined with an Imaging Spectrograph for Routine Raman Spectroscopy" by C. D. Newman et al.; Applied Spectroscopy; vol. 46, No. 2; 1992; pp. 262–265 no month.

"Comparison of Multivariate Calibration Methods for Quantitive Spectral Analysis" by E. V. Thomas et al.; Analytical Chemistry; vol. 62, pp. 1091–1099; May 15, 1990.

"Smoothing and Differentiation of Data by Simplified Least Squares Procedures" by A. Savitzky et al.; Analytical Chemistry, vol. 36, No. 8; pp. 1627–1639 (Jul. 1964).

"NMR and Raman Spectroscopies Move from Lab to Plant" by M. D. Weiss; Today's Chemist at Work, Jan. 1995; pp. 25–28.

"Determination of Petroleum Properties by Fiber–Optic Fourier Transform Raman Spectrometry and Partial Least–Squares Analysis" by C. J. deBakker et al.; Applied Spectroscopy, vol. 49, No. 12, 1995; no month.

"Determination of Octane Numbers and Reid Vapor Pressure of Commercial Petroleum Fuels Using FT–Raman Spectroscopy and Partial Least–Squares Regression Analysis" by J. B. Cooper et al.; Analytical Chemistry; vol. 67 No. 22, Nov. 15, 1995; pp. 4096–4100.

"Remote Fiber–Optic Raman Analysis of Xylene Isomers in Mock Petroleum Fuels Using a Low–Cost Dispersive Instrument and Partial Least–Squares Regression Analysis" by J. B. Cooper et al.; Applied Spectroscopy; vol. 49, No. 5, 1995 no month.

"Near–Infrared Raman Spectroscopy of Liquids and Solids with a Fiber–Optic Sampler, Diode Laser, and CCD Detector." by C. D. Allred et al. *Applied Spectroscopy* vol. 44 No. 7 1990 no month.

OXYGENATE ANALYSIS AND CONTROL BY RAMAN SPECTROSCOPY

CROSS REFERENCE TO RELATED APPLICATIONS

Cross references to related application, 08/432,559, filed May 1, 1995, (attorney docket 6500 AUS) relates to the general field of the present invention.

BACKGROUND OF THE INVENTION

I. Field of the Invention

The invention relates to the determination of the content of specified oxygenated components in a variety of liquids, particularly the concentrations of various alcohols and ethers in hydrocarbon liquids.

Recent U.S. government environmental legislation has resulted in stringent regulatory agency guidelines for product makeup for the chemical and petroleum industries. The guidelines require light control of the chemical composition of these industries' products particularly the composition of gasoline. The oxygenate content of gasoline has received particular attention, with the requirement that reformulated gasolines contain between 2.0 and 2.7 percent by weight of oxygen it is possible to estimate the volume percentage of oxygenate, or the total weight percentage of oxygen in blended gasolines, based on known or estimated blend compositions, level and purity of oxygenate addition. However, it is not always possible to obtain the information required for an accurate calculation. Because it is likely that governmental regulation of the chemical composition of various products and fuels will increase in the future, efficient chemical, refined, and blending operations will require improved analytical procedures to insure compliance with the guidelines.

II. Description of the Prior Art

Prior patents related to the analysis of aromatics in hydrocarbon streams include U.S. Pat. No. 4,963,745 to Maggard, issued Oct. 16, 1990; U.S. Pat. No. 5,223,714 to Maggard, issued Jun. 29, 1993, U.S. Pat. No. 5,243,546 to Maggard, issued Sep. 7, 1993; U.S. Pat. No. 5,145,785 to Maggard and Welch, issued Sep. 8, 1992; international application WO 93/24823, published Dec. 9, 1993.

U.S. Pat. No. 5,349,188 to Maggard, issued Sep. 20, 1994, teaches the determination of octane generally, and U.S. Pat. No. 5,349,189 to Maggard, issued Sep. 20, 1994, teaches the determination of hydrocarbon groups by group type analysis.

Prior art teachings of the determination of oxygenated species can be found in prior literature and patents. A preferred technique is gas liquid chromatography with Oxygen Flame Ionization Detection (OFID), wherein a sample is injected into a partitioning column swept by an elutriating inert gas, e.g., 5% hydrogen in helium. Separated oxygenates in effluent from the partitioning column are converted to carbon monoxide by a cracking reactor, and then to methane by a methanizer. A flame ionization detector detects the several methane bands so produced from each of the oxygenates. The elapsed time for elutriation through the system is measured for the methane band representing each oxygenate. Non-oxygenated hydrocarbons do not interfere with this analysis because they are converted to elemental carbon and deposited on the catalyst contained in the cracker. The OFID procedure and apparatus used for this analysis are illustrated hereinafter in Example 5 and FIG. 4.

Conventionally, the percentages of each of the individual oxygenated compounds is determined in weight percent total oxygen, and volume percent of each oxygenate as required. An example of this procedure is that taught by Wasson ECE Instrumentation, Inc. (1305 Duff Drive Suite 7, Fort Collins, Colo. 80524, Operations Manual Serial Number 930931). Although precise, gas chromatography is time consuming and labor intensive, and the considerable lag time involved can result in unacceptable cost when productions errors occur.

Recently, near-infrared (NIR) spectrophotometric analysis has been used to perform oxygenate analysis. U.S. Pat. No. 5,362,965 to Maggard teaches the determination of oxygenate content in gasolines and other hydrocarbon fuels, with selection of wavelength ranges and data preprocessing to minimize the temperature dependence of the calibrations.

As far back as 1948, Raman spectroscopy was considered for determination of aromatics content in hydrocarbon mixtures (U.S. Pat. No. 2,527,121). For a variety of reasons, however, extensive use of this procedure as a quantitative technique has not occurred to the degree of mid-IR or near-IR absorbance/reflectance spectroscopic methods. One reason for this may be that a significant limitation of Raman spectroscopy has been the presence of interfering fluorescence signals (with the exception of aviation fuel) due to excitation by visible lasers.

Recently, FT-Raman spectrometers have been developed which eliminate the fluorescence problem in many cases by exciting in the NIR spectral region. This capability has sparked renewed interest in the use of Raman spectroscopy in the analysis of petroleum samples. For example, Shope, Vickers and Mann (Appl. Spectrosc., 1988, 42, 468) have demonstrated that when analytes are present in liquid mixtures as minor components, Raman spectroscopy is a viable quantitative technique. Using NIR-FT-Raman spectroscopy in combination with multivariate analysis techniques, Scasholtz, Archibald, Lorber and Kowalski (Appl. Spectrosc., 1989, 43, 1067) have demonstrated that quantitative analysis of percentage of fuel composition is possible for liquid fuel mixtures of unleaded gasoline, super-unleaded gasoline, and diesel fuels. In addition, Williams and co-workers (Anal. Chem., 1990, 62, 2553) have shown that NIR-FT-Raman spectroscopy in combination with multivariate statistics can be used to determine gas oil octane number and octane index. Chung, Clarke, and others have shown that Raman spectroscopy can be used in the quantitative analysis of aviation fuel in the determination of general hydrocarbon makeup, aromatic components, and additives (Appl. Spectrosc., 1991, 45, 1527; J. of Raman Spectrosc., 1991, 22, 79).

Recently, Allred and McCreery described an NIR dispersive Raman instrument utilizing a GaAlAs NIR diode laser, a single-stage imaging spectrograph, CCD detection, and a fiber-optic probe (Appl. Spectrosc., 1990, 44, 1229; Appl. Spectrosc., 1993, 46, 262) for benzene and $KNO_3$ analysis. More recently, Cooper and co-workers have demonstrated (Spectrochimica Acta, 1994, 50A, 567) that low-cost CCD detection is feasible for remote fiber-optic Raman detection. While NIR technique is a viable analytical method for the majority of oxygenated species, the spectral similarity of the oxygenates in the NIR absorbance region make quantitation of individual compounds difficult with NIR when more than one compound is present in significant concentrations. Accordingly, there has remained and for a more effective procedure tier measurement of oxygenates in a variety of liquids, particularly in fuels. The invention addresses this need.

SUMMARY OF THE INVENTION

Accordingly, the invention relates, in one embodiment, to a process for preparing an analytical model for analyzing specified liquid mixtures for the presence and concentrations of certain oxygenated hydrocarbon compounds. Broadly, in this process, multiple samples of liquid mixtures each comprising one or more of certain oxygenates in varying known or determined concentrations are irradiated with near infrared or other radiation, producing scattered Raman radiation omitted from each sample mixture. As used herein, the expressions "known concentration" or "known concentrations" indicate merely that the content of a particular mixture is known or defined, as, for example, by making up the mixture, or by appropriate analysis, which may be before or after the irradiation of the samples. The wavelengths present in the scattered light are characteristic of the molecules present, and the intensity of the scattered light is dependent on their concentrations. The Raman scattered radiation omitted from the respective samples is collected and then dispersed or transformed into spectra with intensities representing the chemical composition of the components of the mixtures of said samples and the concentrations of said components. Multivariate analysis or other mathematical manipulation is performed on some or all of the spectra, or mathematical functions thereof; e.g., to derive a regression model representative of mixtures containing one or more of the specified compositions. The resulting model is useful, as described more fully hereinafter, in analyzing a variety of liquid mixtures, particularly hydrocarbon liquids or mixtures, for the presence and concentrations of oxygenated hydrocarbons.

A variety of oxygenates may be speciated, but the invention is particularly suited to determining the presence and concentrations of alcohols and ethers, more preferably methanol, ethanol, methyl tertiary butyl ether (MTBE), ethyl tertiary butyl ether (ETBE) and tertiary amyl methyl ether (TAME). The model is especially useful for analyzing oxygenate-containing hydrocarbon mixtures, such as petroleum liquids or mixtures, or synthetic petroleum mixtures. Fuels (including reformulated gasolines) may be analyzed as described hereinafter. In one specific aspect of this embodiment, the multiple samples of liquid mixtures, each comprising or containing one or more oxygenates in varying predetermined concentrations, may be prepared as synthetic petroleum mixtures for the analysis. The respective samples of the mixtures are then, as described supra, radiated individually with near-infrared radiation, producing scattered Raman radiation emitted from each sample mixture, and are analyzed in the manner described.

In a second aspect of this embodiment, samples of oxygenate-containing liquid are recovered from a suitable source, such as a chemical plant stream or refinery stream. In a manner similar to that described previously, the respective samples of the mixtures are radiated individually with near-infrared radiation, producing scattered Raman radiation emitted from each sample mixture. Prior or subsequent to irradiation, at least a portion of the samples are analyzed by suitable conventional analysis, such as chromatographic analysis, to determine the nature and concentrations of the various components of interest in the samples. Based on the known concentrations and the spectra obtained, a model is produced, in the manner described previously, this model being based, to great advantage, on actual plant or refinery stream concentrations from the source or site chosen. As will be recognized by those skilled in the art, this procedure can produce an analytical model which eliminates having to perform conventional analysis more than once in the plant or refinery setting.

The use of the models produced, of course, is the great advantage of the invention. Accordingly, the invention, in another embodiment, relates to a process tier determining the concentration of one or more oxygenates, in a specified liquid sample, comprising irradiating the liquid sample with near infrared radiation, producing scattered Raman radiation emitted from said sample. The Raman scattered radiation emitted from the sample is collected, transferred, and dispersed or transformed into spectral intensities corresponding to the chemical composition of the components of the sample and concentration of said components. The concentrations of one or more oxygenates present are then determined by processing the spectral intensities from the sample according to the models previously mentioned, with the proviso or understanding that the source radiation wavelength in this embodiment is the same as or is correlated to that employed in establishing the models. As those skilled in the art will be aware, a sample may be static or dynamic, i.e., may vary over time. The terms "sample" or "samples", in this context, include flowing streams of such mixtures, which are particularly preferred for real-time control of processes in response to frequent analysis according to the invention. Temporal discrimination of a dynamic stream requires that spectra be acquired during a finite time interval. The shorter the interval, the higher temporal resolution of the changing concentration. Thus, spectra may be acquired over a very short time (seconds), or over a longer time (minutes), the term "spectra" herein encompassing also a single spectrum. Again, only selected portions of the spectra obtained need be processed, as will be evident to those skilled in the art; language hereinafter indicating processing of spectra is to be understood to indicate processing of all or of selected spectral regions. The speed of analysis obtainable by the present invention (less than one minute) enables on-line control response times not possible with past prior art chromatographic methods. The determination or different components may be made simultaneously and nearly continuously, providing on-line (or at-line) analysis without the need to return samples to control laboratories in refineries.

The invention thus provides, particularly with the use of modern fiber optics, a quick and efficient method of monitoring the concentration of an oxygenated hydrocarbon, such as MTBE, on-line, and the monitoring system may be coupled, in the most preferred aspects of the invention, with a computer and other equipment to regulate the parameters of a process, e.g., to control the concentration of a particular component, e.g., MTBE, in the liquids, such as hydrocarbon fuels, produced or to feed-forward the compositions of starting materials being fed to a process.

I. General Statement of the Invention

According to the invention, concentrations of oxygenates in various liquids, including hydrocarbon fuels, can be determined with great accuracy, e.g., ±0.2% wt or better, from a remote location using fiber-optic Raman spectroscopy with near-infrared laser excitation, utilizing multivariate regression analysis.

II. Utility of the Invention

This invention will find its greatest application in the petroleum refining industry, the techniques described being useful to monitor and control the amounts of individual oxygenate species in gasoline.

Another preferred application is the regulation of the required oxygenate content for reformulated the in gasoline blending systems using a blending program such as Ashland Petroleum's BOSS™ (Blend Optimization and Scheduling System), Chevron's GINO (Gasoline In-line Optimization), Oil Systems, Inc., MG Blend, or other similar blending optimization programs. Blending systems for use with the present invention, to provide blends having desired species analysis, can be of conventional design, usually involving the use of proportioning pumps or automatic control valves which control the addition rate for each of a series of components fed from different tanks or other sources. A preferred blending system comprises, for example, a system wherein a signal controls the feeding and blending of streams, including one or more which contains an oxygenate, into a common zone, whereby a product having a desired oxygen content is produced. A computer receiving the output signal from the spectrometer used to determine the concentration of a given oxygenate can readily process the information to not only provide the oxygenate analysis in the finished blended hydrocarbon, e.g., gasoline, but also to provide the target blend at minimum cost, given the relative costs or species analysis enhancement values of all streams being fed to the blending system.

BRIEF DESCRIPTION OF THE DRAWINGS

In FIG. 4, detector signal is plotted on the vertical axis as a function of time (in minutes), which is on the horizontal axis.

DETAILED DESCRIPTION OF THE INVENTION

Figure 1:
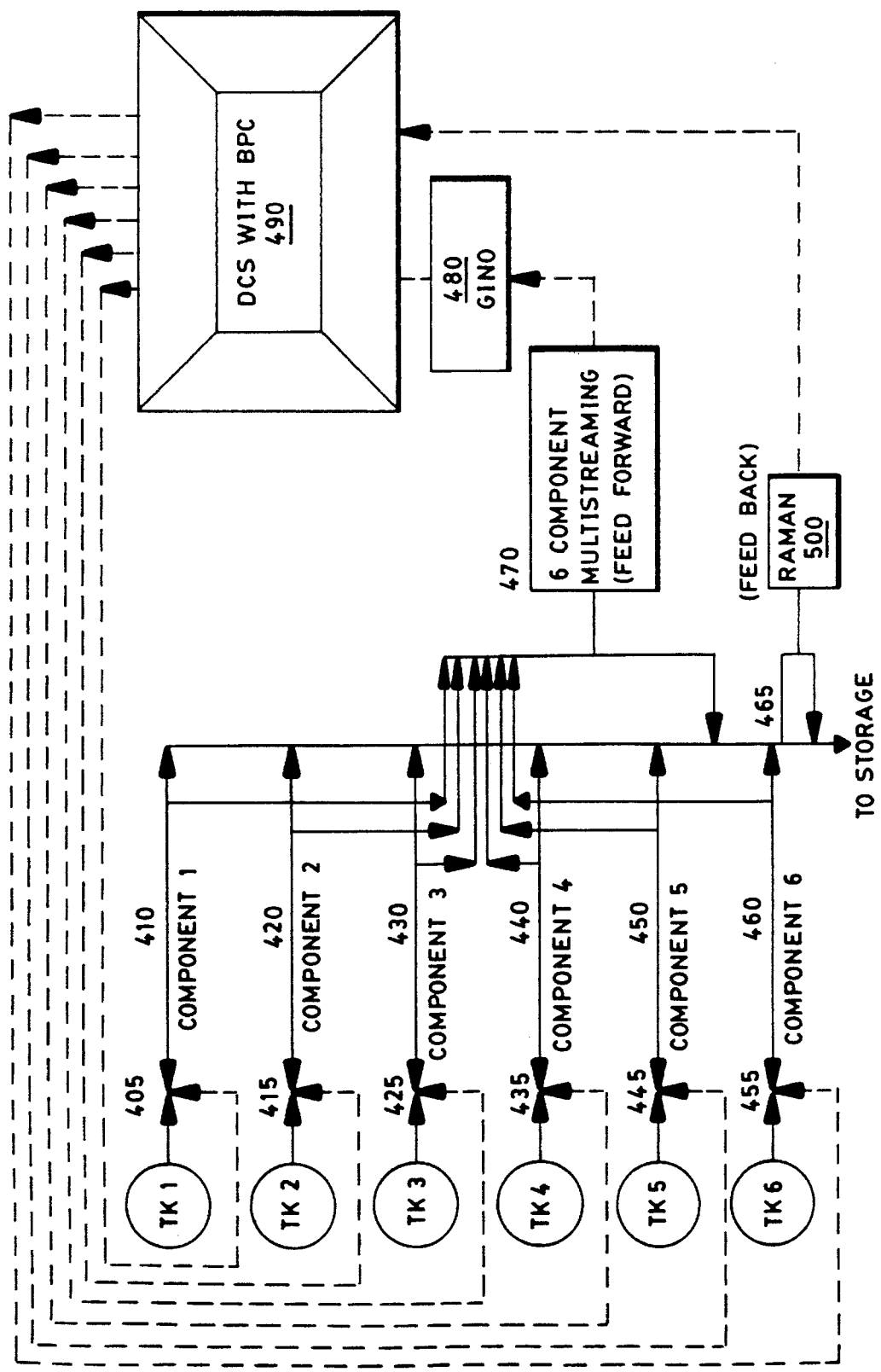
FIG. 1 illustrates schematically the fuel blending process described in Example 1.

The source of radiation used to produce the Raman scattering will be varied according to the liquid treated. In the case of oxygenate-containing liquids (and other non-fluorescing liquids), the type of radiation source may be varied considerably, and a laser of suitable visible wavelength may be used. With petroleum liquids or other fluorescing samples, however, laser systems of near infrared wavelength are preferred. Despite the lower degree of fluorescence obtained by choosing a near-infrared laser, highly colored samples may still fluoresce and interfere with Raman shifts corresponding to the fingerprint ("FP") region (i.e., about 1900–175 $cm^{-1}$). It is still possible to obtain Raman information in the C-H stretch ("CH") region (i.e., about 3300–2500 $cm^{-1}$) using a Fourier Transform spectrometer; and oxygenate determination is still possible. In addition to the spectrometers specifically discussed hereinafter, other suitable dispersive and Fourier Transform spectrometers are available and may be used. The number of samples utilized for the model will vary with the application and desire for accuracy. For example, in the case of a synthetic fuel mixture, from 20 to 50 samples will be adequate, with more or less being used as desired or needed.

In the case of dispersive Raman spectroscopy, if a Fabry-Perot type diode laser is used for laser excitation, "mode hopping" may occur. This may be minimized by keeping the excitation laser, over the course of operations, in constant current mode while its temperature is stabilized. Mode hopping causes frequency shifts or line broadening in the Raman spectra. Since mode hopping of diode lasers is a function of both temperature and drive current, use of a diode laser in constant power mode often forces the drive current into regions of instability at given temperatures, thus inducing a mode hop. Since the spectra may be acquired over a one-minute integration period, the average change in laser intensity while in constant current mode over a total integration period is typically very small. Diode lasers with either internal or external gratings, e.g, distributed Bragg reflector diode lasers, are preferred over Fabry-Perot diode lasers since diode lasers with internal or external gratings eliminate mode hopping.

Table A lists preferred, more preferred and most preferred dispersive Raman spectral regions for determining the components according to the invention. Table B lists preferred, more preferred and most preferred FT-Raman spectral regions for determining specific components according to the invention.

TABLE A

HIGH CORRELATION DISPERSIVE RAMAN SPECTRAL REGIONS

| Component | Units | Preferred | More Preferred | Most Preferred |
|---|---|---|---|---|
| Methanol | $cm^{-1}$ | 3300–2500, 1900–175 | 3127–2733, 1682–959 | 2964–2814, 1477–1014 |
| Ethanol | $cm^{-1}$ | 3300–2500, 1900–175 | 3151–2668, 1535–851 | 2955–2895, 1324–866 |
| 1-propanol | $cm^{-1}$ | 3300–2500, 1900–175 | 3059–2673, 1573–400 | 2958–2858, 1477–446 |
| 2-propanol | $cm^{-1}$ | 3300–2500, 1900–175 | 3079–2681, 1557–323 | 2995–2860, 1473–800 |
| 1-butanol | $cm^{-1}$ | 3300–2500, 1900–175 | 3087–2660, 1657–309 | 2961–2859, 1475–382 |
| 2-butanol | $cm^{-1}$ | 3300–2500, 1900–175 | 3101–2624, 1650–301 | 2990–2861, 1477–481 |
| isobutanol | $cm^{-1}$ | 3300–2500, 1900–175 | 3079–2681, 1557–323 | 2995–2860, 1473–800 |

TABLE A-continued

HIGH CORRELATION DISPERSIVE RAMAN SPECTRAL REGIONS

| Component | Units | Preferred | More Preferred | Most Preferred |
|---|---|---|---|---|
| tert-butanol | $cm^{-1}$ | 3300–2500, 1900–175 | 3070–2690, 1530–300 | 3000–2898, 1470–320 |
| tert-amyl alcohol | $cm^{-1}$ | 3300–2500, 1700–175 | 3070–2690, 1530–300 | 3000–2898, 1470–320 |
| methyl tert-butyl ether (MTBE) | $cm^{-1}$ | 3300–2500, 1900–175 | 3278–2510, 1661–196 | 3011–2791, 892–466 |
| ethyl tert-butyl ether (ETBE) | $cm^{-1}$ | 3300–2500, 1900–175 | 3278–2510, 1661–196 | 3011–2791, 892–466 |
| tert-amyl methyl ether (TAME) | $cm^{-1}$ | 3300–2500, 1900–175 | 3278–2510, 1661–196 | 3011–2791, 892–466 |
| diisopropyl ether (DIPE) | $cm^{-1}$ | 3300–2500, 1900–175 | 3079–2681, 1557–323 | 2995–2860, 1473–800 |

TABLE B

HIGH CORRELATION FT-RAMAN SPECTRAL REGIONS

| Component | Units | Preferred | More Preferred | Most Preferred |
|---|---|---|---|---|
| Methanol | $cm^{-1}$ | 3300–2500, 1900–175 | 3127–2733, 1682–959 | 2964–2814, 1477–1014 |
| Ethanol | $cm^{-1}$ | 3300–2500, 1900–175 | 3151–2668, 1535–851 | 2955–2895, 1324–866 |
| 1-propanol | $cm^{-1}$ | 3300–2500, 1900–175 | 3059–2673, 1573–400 | 2958–2858, 1477–446 |
| 2-propanol | $cm^{-1}$ | 3300–2500, 1900–175 | 3079–2681, 1557–323 | 2995–2860, 1473–800 |
| 1-butanol | $cm^{-1}$ | 3300–2500, 1900–175 | 3087–2660, 1657–309 | 2961–2859, 1475–382 |
| 2-butanol | $cm^{-1}$ | 3300–2500, 1900–175 | 3101–2624, 1650–301 | 2990–2861, 1477–481 |
| isobutanol | $cm^{-1}$ | 3300–2500, 1900–175 | 3079–2681, 1557–323 | 2995–2860, 1473–800 |
| tert-butanol | $cm^{-1}$ | 3300–2500, 1900–175 | 3070–2690, 1530–300 | 3000–2898, 1470–320 |
| tert-amyl alcohol | $cm^{-1}$ | 3300–2500, 1700–175 | 3070–2690, 1530–300 | 3000–2898, 1470–320 |
| methyl tert-butyl ether (MTBE) | $cm^{-1}$ | 3300–2500, 1900–175 | 3278–2510, 1851–196 | 3011–2791, 892–466 |
| ethyl tert-butyl ether (ETBE) | $cm^{-1}$ | 3300–2500, 1900–175 | 3278–2510, 1661–196 | 3011–2791, 892–466 |
| tert-amyl methyl ether (TAME) | $cm^{-1}$ | 3300–2500, 1900–175 | 3278–2510, 1661–196 | 3011–2791, 892–466 |
| diisopropyl ether (DIPE) | $cm^{-1}$ | 3300–2500, 1900–175 | 3079–2681 1557–323 | 2995–2860, 1473–800 |

Correlation of the spectra to the species concentrations of interest is accomplished using multivariate analysis. As utilized herein, the form "multivariate analysis" is understood to include all types of multivariate statistical analysis, with the procedures known as partial least squares (PLS), principal component regression (PCR), multiple linear regression (MLR) by classical or inverse least squares being preferred. MLR, PCR and PLS can be performed without any data preprocessing, or (alternatively), using several different data preprocessing techniques including: derivative (Savitzky and Golay, Anal. Chem 1964, 36, 1627), normalization, mean centering, variance scaling, autoscaling (mean-centering followed by variance scaling), and range scaling. Calibrations may also be made based on Raman intensity differences, whereby the intensity spectrum for a blendstock prior to oxygenate addition, is subtracted from the intensity spectrum of the same blendstock after the oxygenate is added. Using a single-beam instrument with data storage capability, a spectrum of the unoxygenated blendstock may be acquired for use as the reference, prior to running the samples. This technique is especially useful when undesirable interferences are present in spectral regions used in the calibrations. Spectral subtraction was used by Tackett, U.S. Pat. No. 5,412,581, liar double-beam, NIR measurements of physical properties of hydrocarbons, with a reference hydrocarbon placed in the reference beam. Care was taken in the instrument design to ensure that the sample and reference cells were maintained at the same temperature. This was necessary to eliminate any artifacts due to the temperature dependence of NIR measurements. Raman measurements are not affected by temperature, providing an additional advantage to the use of the Raman technique for such measurements.

By the MLR method, a Raman analyzer determines the concentration or other property of interest for the sample, based on calibrations which set forth in the equation below, the constants $k(0), k(1), k(2), \ldots, k(m)$, for m wavenumbers at which Raman intensity is measured:

$$\text{Value of Interest} = k(0) + k(1) \times f(A_1) + k(2) \times f(A_2) + \ldots + k(m) \times f(A_m)$$

Where k(0)=bias coefficient k(i)=coefficient for wavenumber i $f(A_i)$=Raman intensity, a derivative of intensity with respect to wavenumber, or some other function of the intensity at wavenumber i, for i=1, 2, . . . , m (wavenumbers 1, 2, . . . , m).

By the PCR method, each spectrum (or one or more portions) in the calibration sample set is represented as an n-dimensional vector, where n is the number of points to be used in each spectrum. To each point is associated a wavenumber at which Raman intensity was measured. Each vector is broken down into one or more components, plus an error vector to account for variation not explained by the components. By this mathematical treatment or "decomposition," the spectrum is represented as the weighted vector sum of the components plus the error vector. Each successive component accounts for the variation remaining in the calibration set, after subtracting the weighted contributions of all preceding components. The coefficients in the weighted sums (also known as "scores") are then correlated with the properties of interest (i.e., species concentrations) using multilinear regression. PLS is similar to PCR in that the spectra are decomposed in components ("latent variables"). However, by the PLS method, the spectra are weighted by the species concentrations prior to the decomposition step. The regression is accomplished during the decomposition, making a separate regression step unnecessary. There are two PLS methods in common use: PLS-1, which calculates a separate set of scores for each species concentration; and PLS-2, which, as does PCR, calculates a single set of scores for all species of interest. More detailed information on these methods can be found in the literature (Geladi, P. and B. R. Kowalski, Partial Least-Squares Regression: A Tutorial, Anal. Chim. Acta 1986, 185, 1–17).

A cross validation of the data is used to evaluate the quality of the calibration by leaving out one spectrum at a time while performing a partial least squares regression on the remaining spectra and using the resultant regression to predict the value for the left-out spectrum. Alternatively, spectra for a separate set of samples not included in the calibration set, may be used for independent validation.

Outlier diagnostics (Thomas and Kaaland, Anal. Chem. 1990, 62, 1091) are used to generate leverage plots for the different spectra for each partial least squares regression analysis. The leverage of each spectral sample is indicative of how much of an effect each sample has on influencing the regression model. The leverage plots are useful for detecting artifacts (due to mode hopping, back-scattering of Raman modes from the excitation fiber into the collection fiber, cosmic rays or sampling errors).

Results from MLR, PLS or principal component analysis can be used directly or incorporated into a neural network to obtain the final model. Neural networks are discussed in several publications, including Long, J. R., V. G. Gregoriou, and P. J. Gemperline, Anal. Chore. 1990, 62, 1791–1797. Use of PCA and PLS scores as inputs to neural networks are discussed by Borggaard, C. and H. H. Thordberg (Anal. Chore. 1992, 64, 545–551).

As indicated, the procedures of the invention are applicable to any liquid mixture containing one or more oxygenates. However, the invention is most adapted to use with petroleum mixtures, such as gasolines, aviation libel, and diesel fuels. As used herein, the term "synthetic fuel mixture" means a prepared mixture of refinery components to cover the composition range in actual fuel blends.

DESCRIPTION OF THE PREFERRED EMBODIMENTS

EXAMPLE 1

(Invention Controlling a Fuel Blender)

FIG. 1 represents a control scheme for an on-line blender in a refinery, with both feed-forward and feedback control loops, utilizing Raman spectral analysis of oxygenate levels to provide control.

In FIG. 1, the use of multistreaming, whereby the component streams are switched sequentially to a single probe, using valves, is illustrated. However, multiplexing, whereby a probe is located at each control point, or a combination of both, can also be used. In a multistreaming operation such as that illustrated in FIG. 1, component streams 410, 420, 430, 440, 450 and 460 are sequentially routed to the sample cell or sample in line probe of Raman spectrometer 470 which analyzes each stream for properties or components of interest, e.g., wt % oxygen. An output signal for each stream (proportional to wt % oxygen) is then transmitted to optimizing software such as GINO. The GINO software, resident in blending computer 480, then continuously analyzes the signal, optimize and update the blend recipe in response thereto, and downloads the updated recipe to Blend Ratio Control (BRC) software which is resident in Distributed Control System (DCS) 490. The BRC software is capable of controlling DCS 490 which in turn may adjust the position of valves 405, 415, 425, 435, 445, and 455 to change the flow rates of component streams 410, 420, 430, 440, 450 and 460, respectively.

Another Raman spectrometer 500 can also be used in a feedback mode. That is, a slip stream 465 of the finished blend is directed to the sample probe or sample cell of Raman spectrometer 500, which analyzes the finished blend for wt % oxygen and other components of interest. DCS 490 then receives the feedback signal from Raman spectrometer 500 in the same manner as it receives the feed-forward signals from Raman spectrometer 470. The DCS 490 is configured to allow direct control of valves 405, 415, 425, 435, 445 and 455 by the feedback control loop to override the recipe established by the feed-forward control loop when necessary.

Raman spectrometer 500 may be the same instrument as Raman 470, with feed-forward and feedback functions operating in a multiplexing or multistreaming mode.

In each the following examples 2 through 4, a model is formulated, utilizing the sampling and multivariate analysis procedure described herein, for the liquid or liquids to be monitored. As will be appreciated by those skilled in the art, in the individual processes described, a radical change in liquid content, as for example, the substitution of a substantially different feedstock, e.g., substitution of oil shale liquid for Arabian light, would require derivation of a new model representing the ranges of variation of that feed.

EXAMPLE 2

(Oxygen levels by Dispersive Raman Spectroscopy PLS Calibration)

Figure 2:
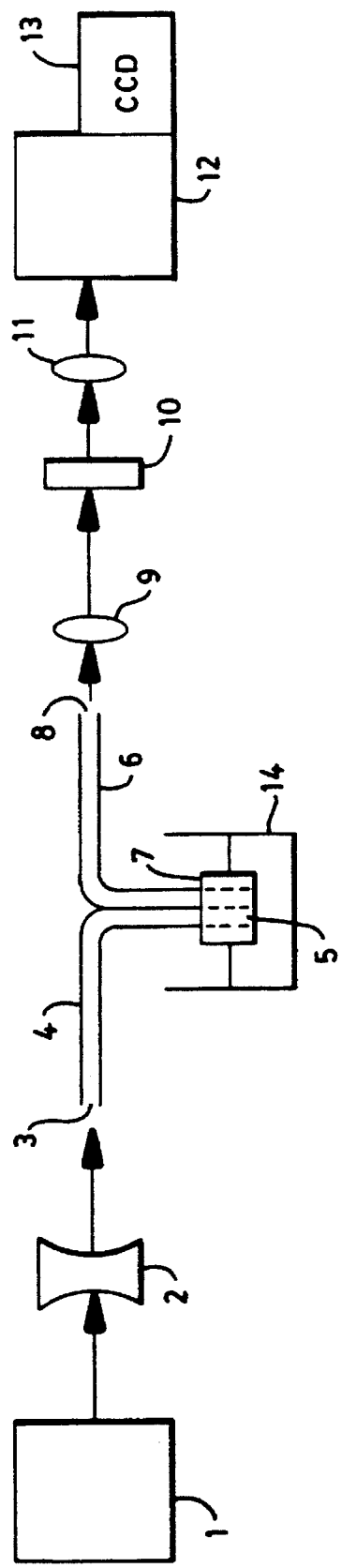
FIG. 2 of the drawing schematically illustrates a suitable Dispersive Raman apparatus, with fiber optic probe, for carrying out embodiments of the invention.

In order to describe the invention more fully, reference is made to FIG. 2. The setup shown is analogous to that described in the aforementioned McCreery et al publication, which is hereby incorporated by reference. Accordingly, there is shown a radiation source 1, in this case a GaAIAs DBR diode laser (Spectra Diode Labs) which emits radiation in the near infrared. The radiation is filtered with dielectric band pass filter 2 (Janos) and is sent into the proximal end 3 of the excitation fiber 4 (200 micron quartz fiber optic, Polymicro). The probe tip 5 consists of the distal ends of the excitation fiber 4 and a parallel collection fiber 6, both fibers being sealed into a stainless steel tube 7 with epoxy and the ends polished. At the probe tip 5, the laser energy exits the excitation fiber 4 and the Raman scattered light thus produced is collected by the distal end of the parallel collection fiber optic 6. Light from the proximal end 8 of the collection fiber 6 is collimated with an f/2 plano-convex NIR reflection coated lens 9 and then filtered with a 850 nm holographic notch filter 10 (Kaiser Optical) to remove Rayleigh scattering before focusing the Raman signal with an f/4 lens 11 onto the slits (60 micron slit width) of an image corrected ¼ meter spectrograph 12 (Chromcx). A 300 groove/mm grating blazed at 1 micron was used to disperse the Raman signal. A ST6UV charge coupled detector (CCD) 13 (Santa Barbara Instruments Group) thermoelectrically cooled to −35 C was used to detect the dispersed signal. The detector 13 consists of 750 horizontal pixels (12 micron widths)×350 vertical pixels. The pixels are binned on chip by two in the horizontal direction and by 350 in the vertical direction giving a total of 375 superpixels. According to the invention, Raman spectra are acquired by placing the probe tip 5 directly into a sample which is provided in container or vessel 14 and integrating over 60 seconds for a size perspective, the fiber-optic length for fiber 4 is 2 meters from the laser to the probe tip, and the length of fiber 6 is 3 meters from the probe tip to the spectrograph 12.

All spectra are recorded the same day over a four hour period during which the diode laser setting (805 nm) remains constant and the room temperature remains constant at 23° C. The incident power from laser 1 at the sample is ~50 mW, and the spectral resolution for the described system is ~10 cm$^{-1}$. Spectral processing and partial least squares regression analysis are performed using Pirouette multivariate software (Infometrix) or QuantIR (Nicolet). Values for wt % oxygen were calculated based on oxygenate addition levels.

In the case of probes which utilize lengthy fibers, e.g., several meters, a second dielectric band pass filter will be required near the distal end of excitation fiber 4. For example, approximately one-half meter from the distal end of excitation fiber 4, the fiber may be cleaved, and the laser beam may be collimated with a lens, directed through a band pass filter, and refocused with a second lens into the other cleaved end of excitation fiber 4.

Table C is a statistical summary for Dispersive Raman PLS calibrations for ethanol and MTBE in synthetic gasoline mixtures. Calibration weight percentage values for calibration were determined by calculation from oxygenate addition levels. Listed for each calibration are number of calibration standards, number of PLS factors, Standard Error of Validation, wavenumber range and range of data for each component.

TABLE C

Summary of PLS Factors for Dispersive Fiber-optic Raman of Ashland Petroleum Synthetic Gasoline Mixtures

| Species | Calibration | # of Standards | # of Factors | SEV[1] (Wt % or Vol %) | Wave-number Range (cm$^{-1}$) | Range of Data (Wt % or Vol %) |
| --- | --- | --- | --- | --- | --- | --- |
| Ethanol | Wt % Oxygen | 10 | 4 | 0.377 | 1534.5–851.8 | 0.000–4.486 |
| Ethanol | Vol % Ethanol | 10 | 4 | 1.14 | 1534.5–851.8 | 0.00–12.00 |
| MTBE | Wt % Oxygen | 36 | 5 | 0.244 | 1661.0–685.9 | 0.3594–3.2026 |

[1]SEV is the square root of the sum of the squares of the residuals divided by (n − k − 1), where n is the number of standards in the model and k is the number of factors in the model. Performed using "leave one out" technique.

Similarly, calibrations may be made for other oxygenates commonly found in hydrocarbon fuels, including such species as methanol, tertiary butyl alcohol (TBA), ethyl tert-butyl ether (ETBE), tertiary amyl methyl ether (TAME), diisopropyl ether (DIPE), and other oxygen-containing hydrocarbons.

EXAMPLE 3

(Oxygen levels by FT-Raman Spectroscopy—PLS Calibration)

Figure 3A:
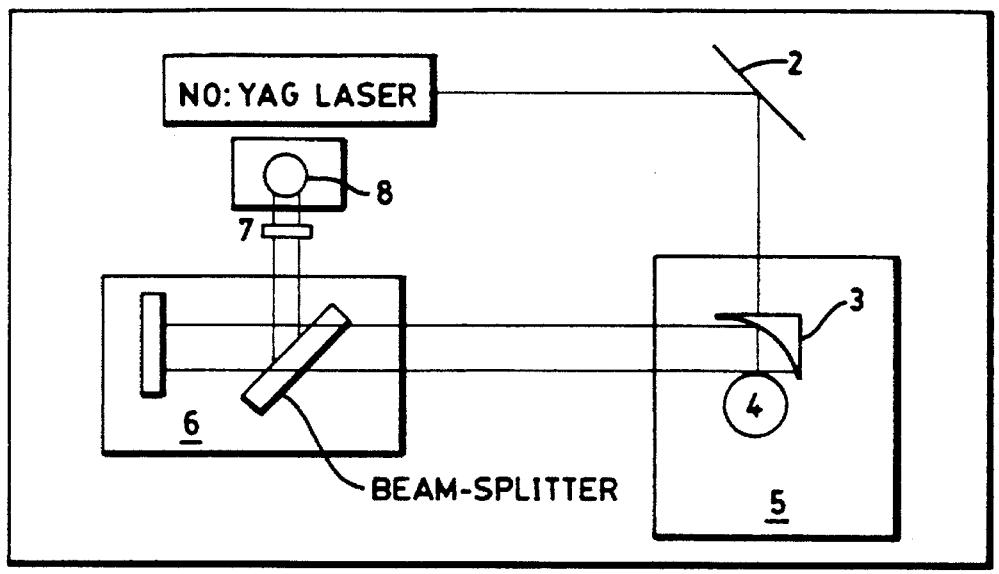
FIG. 3a schematically illustrates a suitable FT-Raman apparatus for carrying out embodiments of the invention.
Figure 3B:
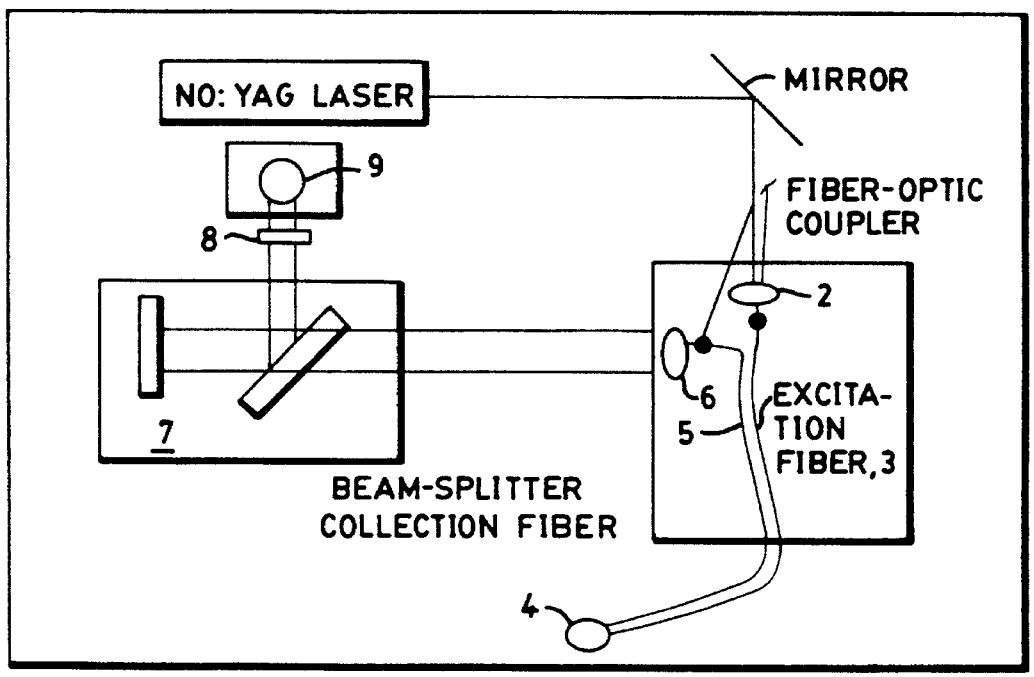
FIG. 3b schematically illustrates a suitable FT-Raman apparatus, equipped with a fiber optic probe, for carrying out embodiments of the invention.

Alternatively (FIG. 3), a FT-Raman (Fourier transform, near-infrared, Raman spectrometer) may be used, wherein the grating is replaced by a Michelson interferometer or other device capable of producing an interferogram from the Raman scattered light from the sample. By appropriate software, the Fourier transform of the interferogram is calculated to produce the spectrum. In the FT-Raman spectrometer, shown in 3a, the petroleum sample 4 in a glass container is placed in a holder in compartment 5. The sample is then irradiated with near infrared radiation (wavelength 1064 nm) from a Nd:YAG laser 1, using mirror 2, through an opening in parabolic collection mirror 3. Mirror 3 collects the scattered Raman and Rayleigh radiation at 180 degrees and collimates it for optimum collection efficiency. The collimated beam is sent to interferemeter 6, filtered with a holographic notch filter 7 (to remove the Rayleigh scattered laser light) and finally detected by a high-purity, germanium detector 8.

Alternatively, the FT-Raman spectrometer can be coupled to a fiber-optic probe for remote sampling. In this configuration (FIG. 3b), the laser beam from laser 1 is focused by lens 2 into the proximal end of excitation fiber 3. The distal end of excitation fiber 3 delivers the laser radiation to the remote sample 4. The Raman and Rayleigh scattered light is then collected by a collinear collection fiber 5 which delivers the radiation back to the spectrometer. The radiation exits the collection fiber 5 and is collimated by lens 6. As before, the collimated beam is sent to interferometer 7, filtered by holographic notch filter 8, and detected by detector 9.

In the case of probes which utilize lengthy fibers, e.g., several meters, a dielectric band pass filter will be required near the distal end of excitation fiber 3. For example, approximately one-half meter from the distal end of excitation fiber 3, the fiber may be cleaved, and the laser beam may be collimated with a lens, directed through a band pass filter, and refocused with a second lens into the other cleaved end of excitation fiber 3.

The spectra of both configurations are substantially the same with the exception that the fiber-optic configuration results in a slightly lower intensity signal. Although FIGS. 1 and 2 illustrate the use of single fiber excitation and collection, those skilled in the art will appreciate that multiple fiber excitation and collection, with the optic fibers properly angled is preferred, such equipment being known.

Table D is a statistical summary for FT-Raman calibrations for ethanol and MTBE in synthetic gasoline mixtures. Listed for each calibration are number of calibration standards, number of PLS factors, Standard Error of Validation, wavenumber range and range of data for each component. Calibration weight percentage values for calibration were determined by calculation from oxygenate addition levels.

formed on intensities or their first derivatives at the wavenumbers indicated in Table E, for Raman spectra collected using the procedure and apparatus described previously in Example 3. For the MTBE calibrations, additional samples without oxygenate were included in the calibrations, for a total of 155 calibration samples. Calibrations were made using the fingerprint region (1900–175 cm–1), the C-H stretch region (3300–2500 cm$^{-1}$), or both (indicated respectively by "FP", "CH", or "both" in Table E).

TABLE D

Summary of PLS Factors for FT-Raman of Ashland Petroleum Synthetic Gasoline Mixtures

| Species | Calibration | # of Standards | # of Factors | SEV[1] (Wt % or Vol %) | Wave-number Range (cm$^{-1}$) | Range of Data (Wt % or Vol %) |
|---|---|---|---|---|---|---|
| Ethanol | Wt % Oxygen | 10 | 5 | 0.345 | 3150.6–2669.4, 1534.5–851.8 | 0.00–4.486 |
| Ethanol | Vol % Ethanol | 10 | 4 | 0.87 | 3150.6–2668.4, 1534.5–851.8 | 0.00–12.00 |
| MTBE | Wt % Oxygen | 77 | 4 | 0.143 | 3277.9–2510.3, 1850.8–196.1 | 0.182–3.288 |

[1]SEV is the square root of the sum of the squares of the residuals divided by $(n - k - 1)$, where n is the number of standards in the model and k is the number of factors in the model. Performed using "leave one out" technique.

Similarly, calibrations may be made for other oxygenates commonly found in hydrocarbon fuels, including such species as methanol, tertiary butyl alcohol (TBA), ethyl tert-butyl ether (ETBE), tertiary amyl methyl ether (TAME), diisopropyl ether (DIPE), and other oxygen-containing hydrocarbons.

EXAMPLE 4

(Oxygen Levels by FT-Raman Spectroscopy—MLR Calibration)

Table E is a statistical summary for FT-Raman MLR calibrations for ethanol and MTBE in synthetic gasoline mixtures. A multiple linear regression analysis was per- Also shown in Table E for each calibration are number of calibration standards, wavenumbers used, coefficient of determination ($R^2$), Standard Error of Estimate, pretreatment method, and range of data for each component (calculated for this calibration set by conventional well-known statistical techniques).

TABLE E

Summary of MLR Calibration for FT-Raman of Ashland Petroleum Synthetic Gasoline Mixtures

| Species | Calibration | # of Standards | Region (FP or CH): Wave-numbers used (cm$^{-1}$) | R squared | SEE[1] (Wt % or Vol %) | Pretreatment Method | Range of Data (Wt % or Vol % |
|---|---|---|---|---|---|---|---|
| Ethanol | Wt % Oxygen | 10 | FP: 886.5, 1303.1 | 0.9986 | 0.068 | none | 0.000–4.486 |
| Ethanol | Wt % Oxygen | 10 | CH: 2915.3 | 0.9777 | 0.247 | none | 0.000–4.486 |
| Ethanol | Wt % Oxygen | 10 | Both: 2915.3, 963.5 | 0.9954 | 0.120 | none | 0.000–4.486 |
| Ethanol | Vol % Ethanol | 10 | FP: 1303.1, 886.5 | .9984 | 0.19 | none | 0.00–12.00 |
| Ethanol | Vol % Ethanol | 10 | Both: 2934.6, 890.4 | .9982 | 0.20 | none | 0.00–12.00 |

TABLE E-continued

Summary of MLR Calibration for FT-Raman
of Ashland Petroleum Synthetic Gasoline Mixtures

| Species | Calibration | # of Standards | Region (FP or CH): Wavenumbers used (cm$^{-1}$) | R squared | SEE[1] (Wt % or Vol %) | Pretreatment Method | Range of Data (Wt % or Vol % |
| --- | --- | --- | --- | --- | --- | --- | --- |
| MTBE | Wt % Oxygen | 156 | FP: 728.4, 535.5 | .9914 | 0.090 | none | 0–3.2616 |
| MTBE | Wt % Oxygen | 156 | CH: 2811.1, 2830.4 | .9829 | 0.128 | first derivative | 0–3.2616 |

[1]SEE is the Standard Error of Estimate, or the root mean square value for deviations between results by the calibration and those by the primary method, for samples in the calibration set.

Two separate sets of spectra (from five fluorescing samples and from 51 non-fluorescing samples) are used as prediction sets for validation of the two MTBE wt % oxygen calibrations described in Table E, the first calibration being based on the FP region, and the second being based on the CH stretch region. Samples used in the prediction sets were not included in the calibrations. For both calibrations, the same pretreatment used for the calibration is applied to the prediction sets. The intensities (or pretreatment functions thereof) are then used as independent variables in the multiple linear regression equations obtained from the calibration set. The intensity or pretreatment fiction value at each wavenumber is multiplied by its respective weighting constant, and the products are summed with the bias constant to provide a weighted value which is characteristic of the predicted weight percentage of oxygen. Both sample sets are used to validate both calibrations, tier a total of four validations. Table F contains the results as measured by the Standard Error of Prediction (SEP), which is the root mean square value for deviations between results by the calibration and those by the primary method, for samples not in the calibration set.

For the non-fluorescing prediction set, it can be seen in Table F that there is good agreement between actual values and those predicted by the calibration, as indicated by the standard errors of prediction for both the FP and the CH calibrations. The standard errors of prediction for the fluorescing prediction set show that fluorescence interferes severely with the FP calibration. However, even when the samples fluoresce, it is seen that the CH calibration with first derivative pretreatment can be used with satisfactory results.

TABLE F

Validation of MTBE Weight Percent Oxygen Calibrations

| Validation (Prediction) Sample Set | Calibration Wave numbers | Standar Error of Prediction (SEP) |
| --- | --- | --- |
| Non-fluorescing | FP: 728.4, 535.5 | 0.1230 |
| Non-fluorescing | CH: 2811.1, 2830.4 | 0.1835 |
| Fluorescing | FP: 728.4, 535.5 | 5.7033 |
| Fluorescing | CH: 2811.1, 2830.4 | 0.1299 |

Similarly, calibrations may be made for other oxygenates commonly found in hydrocarbon fuels, including such species as methanol, tertiary butyl alcohol (TBA), ethyl tert-butyl ether (ETBE), tertiary amyl methyl ether (TAME), diisopropyl ether (DIPE), and other oxygen-containing hydrocarbons.

EXAMPLE 5

(Comparative with Species Analysis Using Conventional Gas Liquid Chromatography)

Figure 4:
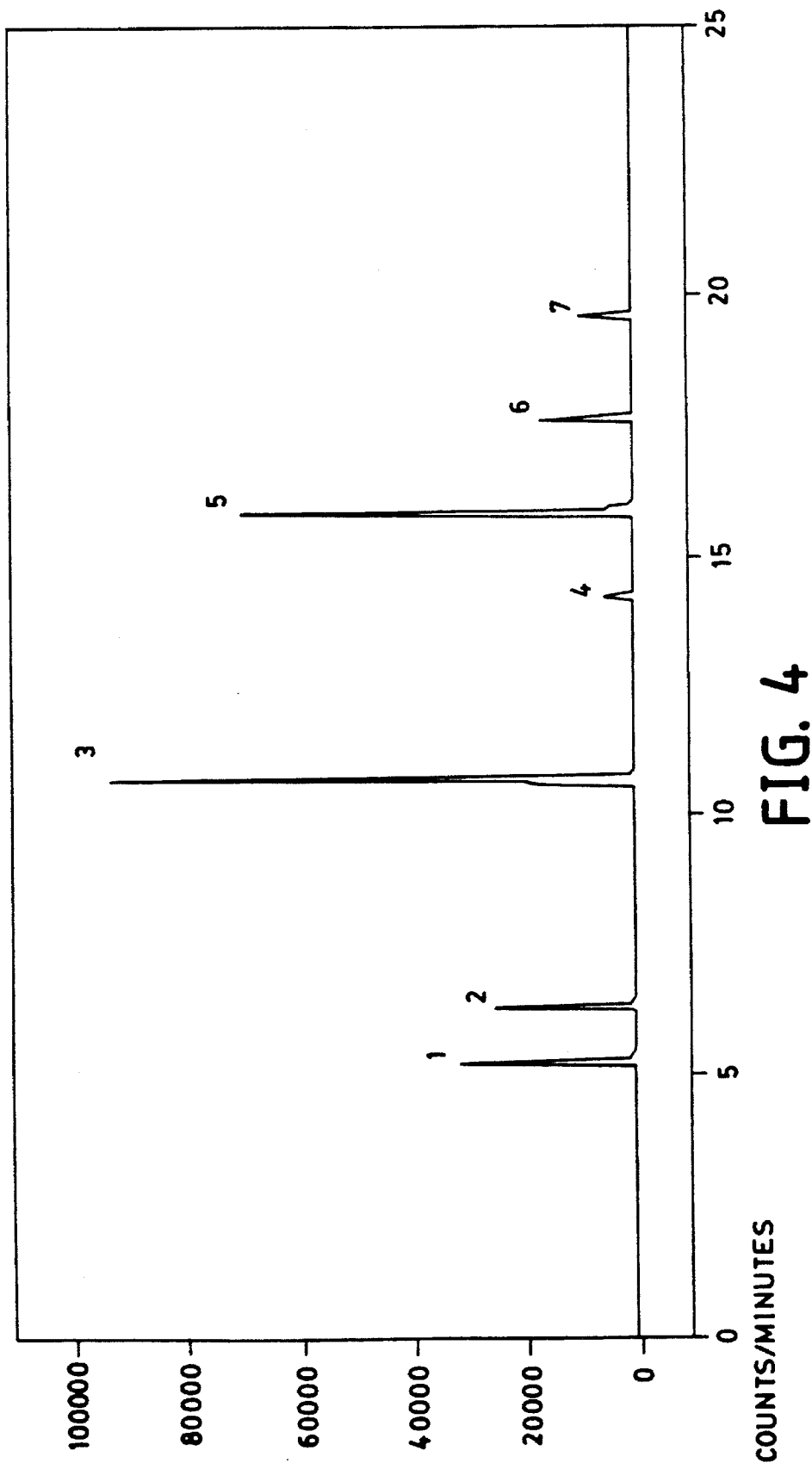
FIG. 4 illustrates an OFID chromatogram of a typical gasoline spiked with several oxygenates and an internal standard for use as a standard sample to calibrate the chromatograph for oxygenate analysis by the prior art chromatographic technique of Example 5.

The chromatogram for a synthetic gasoline mixture containing five oxygenates used in gasoline blending, is shown in FIG. 4, was obtained using a Hewlett Packard Model 5890 temperature programmed gas chromatograph with a methyl silicone capillary column (fused silica, 60M×0.25 mm i.d., df=0.1 uM), and a Wasson ECE OFID detector consisting of a cracker, methanizer and a flame ionization detector Chromatographic conditions were adjusted according to the standard methods established by the instrument manufacturer and Wasson ECE Instrumentation, Inc. This prior art method is useful for the determination of individual species as well total wt % oxygen, and can serve as the primary method for calibration of the Raman instruments used in the present invention. However, as shown by the time elapse in FIG. 4, this method is slow. FIG. 4, is an OFID chromatogram of a typical gasoline spiked with five oxygenates and an internal standard. Retorting to FIG. 4, the order for elution of the peaks is: Methanol 1; Ethanol 2; MTBE 3; ETBE 4; 1,2-Dimethoxyethane (internal standard) 5; TAME 6; and artifact 7. The elutriation time for the last fractions is about 20 min, a much slower analysis time as contrasted to an analysis time of less than one minute for on-line Raman analysis. The OFID procedure requires sample weighing and running of each sample in duplicate. Also, a predetermined amount of an internal standard of known oxygenate content must be added manually to each sample. Finally, a quality control standard must be run by this method every 12 hours or after every set of five duplicate samples, whichever occurs first, according to Federal Register Vol. 59 No. 32 (Feb. 16, 1994), Section 80.46, paragraph g (oxygen and oxygenate analysis), p. 7828. The OFID method is thus seen to be too slow for efficient use in closed loop control for many refinery processes.

EXAMPLE 6

(Illustrations of Raman Spectra for some Oxygenates of lnterest)

Figure 5:
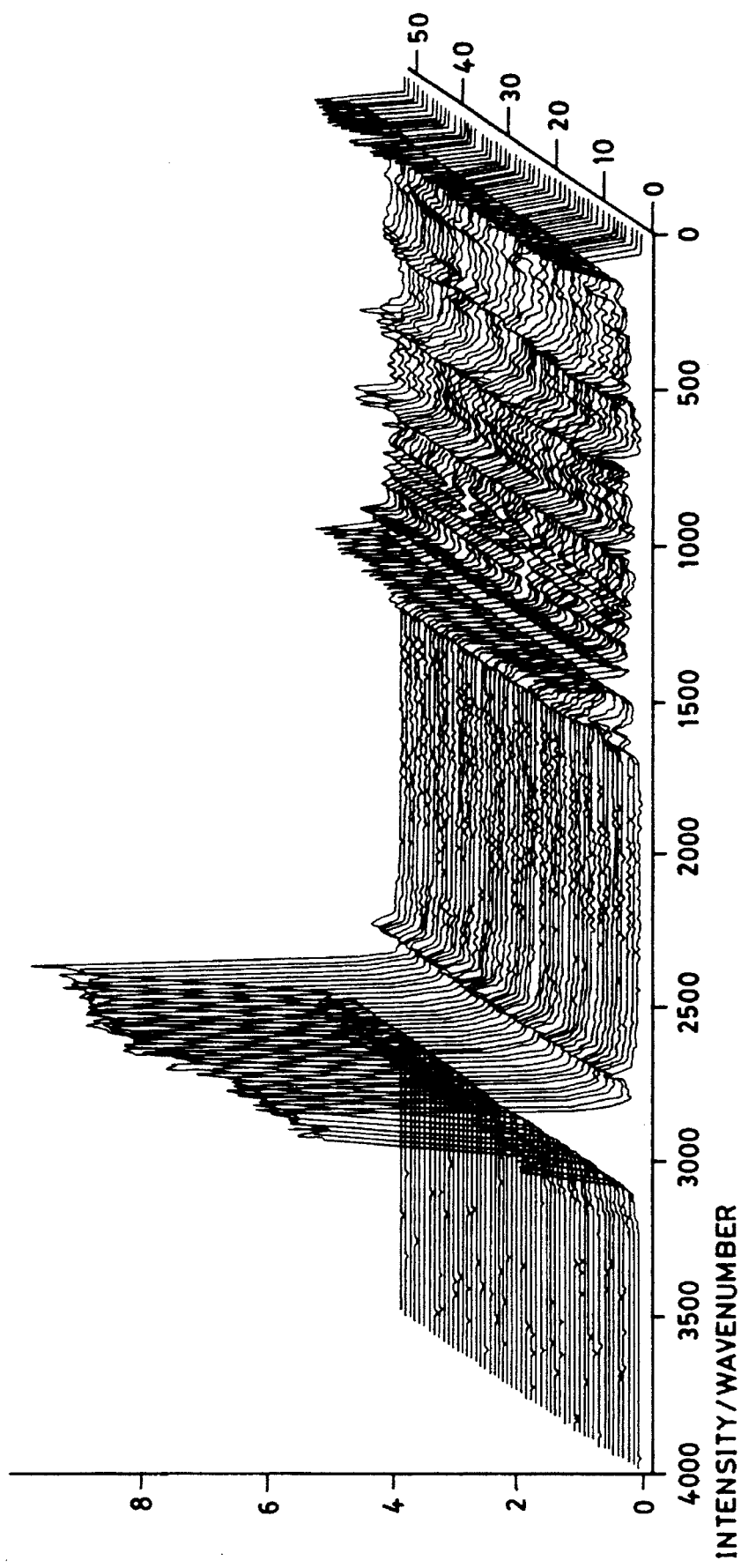
FIG. 5 contains FT-Raman spectra for fifty-one non-fluorescing MFBE gasoline samples used as a validation set in Example 4, for statistical analysis of calibrations.

FIG. 5 contains Raman spectra for the fifty-one non-fluorescing samples used for validation in Example 4. It can be seen that both the CH region and the FP region is suitable for quantitative analysis. Of particular interest in these spectra is a Raman band at 728.4 cm$^{-1}$, characteristic of symmetric O-CC$_3$ stretching. This band shows a strong correlation with wt % oxygen in gasoline blends containing MTBE (R=0.9514, SEE=0.299 wt % oxygen).

Figure 6:
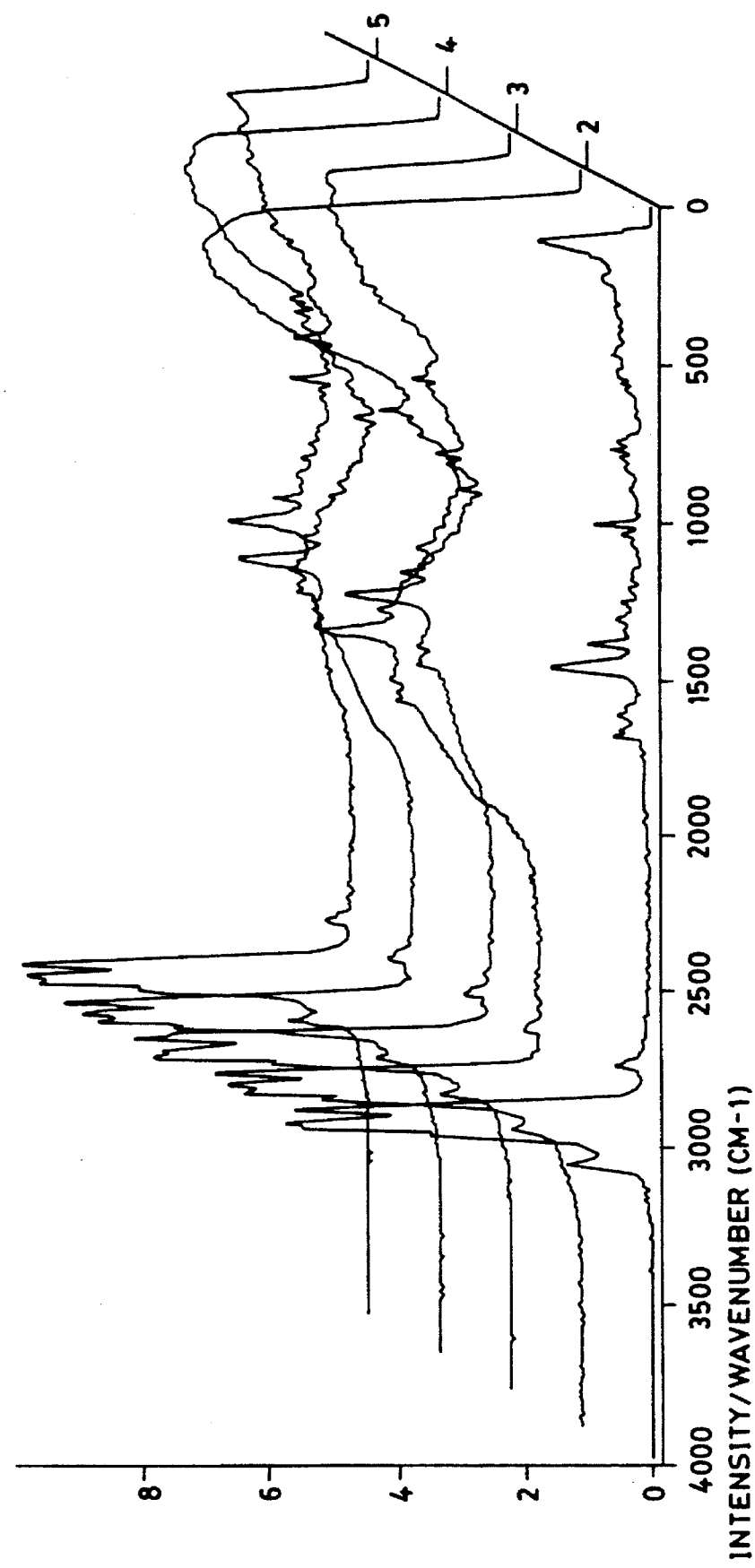
FIG. 6 contains FT-Raman spectra for five fluorescing MTBE gasoline samples used as a validation set in Example 4, for statistical analysis of calibrations.

FIG. 6 contains Raman spectra for the five fluorescing samples used for validation in Example 4. It can be seen in FIG. 6 that fluorescence interferes significantly in the FP region, but only slightly in the CH region. It can be seen by this illustration and by the standard errors of prediction in Table F for fluorescing validation samples, that calibrations based on the CH region provide an alternative when calibrations based on the FP region cannot be used when fluorescence is present.

Figure 7:
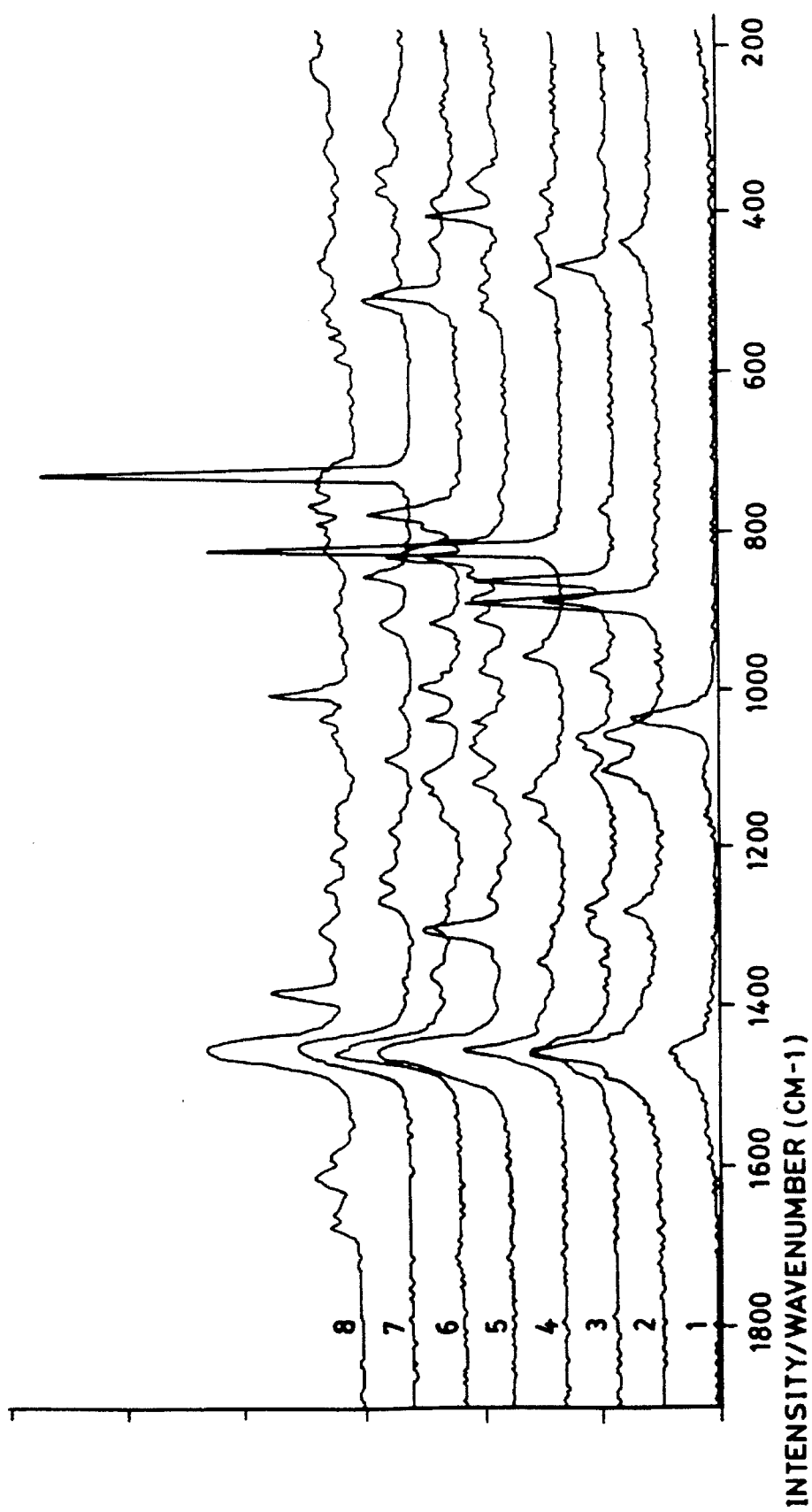
FIG. 7 contains FT-Raman spectra (fingerprint region) for methanol, ethanol, 1-propanol, 1-butanol, 2-propanol, MTBE and 2-butanol.

FIG. 7 contains the fingerprint regions of the FT-Raman spectra for seven oxygenates and (for reference) a spectrum for a typical, regular-grade gasoline with no oxygenate. Included in FIG. 7, are methanol spectrum 1, ethanol spectrum 2, 1-propanol spectrum 3, 2-propanol spectrum 4, 1-butanol spectrum 5, 2-butanol spectrum 6, and MTBE spectrum 7, and gasoline spectrum 8. Referring to FIG. 7, it is seen that distinct features are present in the spectra, particularly in the FP region. Unique features in each oxygenate spectrum, not present in the gasoline spectrum, enable the creation of calibration models capable of distinguishing various oxygenates.

Modifications

Though fundamental bands have been recited, overtones and derivatives of both overtones and fundamental bands may sometimes be substituted if of sufficient strength. This invention can control other refinery and chemical process units, e.g., MTBE, and can also be part of a simultaneous on-line determination of several species and properties (e.g., research and motor octane, benzene, aromatics, etc.).

Specific compositions, methods, or embodiments discussed are intended to be only illustrative of the invention disclosed by this specification. Variations on these compositions, methods, or embodiments are readily apparent to a person of skill in the art based upon the teachings of this specification and are therefore intended to be included as part of the inventions disclosed herein. For example, surface-enhanced Raman, ultraviolet-Raman and Hadamard transform Raman techniques can also be used.

Reference to documents made in the specification is intended to result in such patents or literature being expressly incorporated herein by reference.

What is claimed is:

1. A process comprising:
   a) irradiating a sample of a liquid mixture consisting essentially of liquid hydrocarbons and comprising one or more oxygenated component to produce Raman scattered radiation emitted from the sample;
   b) collecting Raman scattered radiation emitted from the sample;
   c) dispersing or transforming the collected Raman scattered radiation from the sample into spectra with intensities corresponding to the concentration of components of the mixture;
   d) processing said spectra according to a regression model derived by multivariate analysis of Raman spectra, or a mathematical function of Raman spectra, of liquid mixtures containing known concentrations of one or more oxygenated hydrocarbons, to produce a control signal representative of the concentration of an oxygenated component in said mixture;
   e) controlling a process in response to said control signal.

2. A process according to claim 1 wherein said oxygenated hydrocarbon comprises methanol and wherein said collected Raman scattered radiation from the sample is measured in the range of frown about 2964–2814 and/or 1477–1014 nm.

3. A process according to claim 1 wherein said oxygenated hydrocarbon comprises 1-propanol and wherein said collected Raman scattered radiation from the sample is measured in the range of from about 2958–2858 and/or 1477–446 nm.

4. A process according to claim 1 whereto said oxygenated hydrocarbon comprises 2-propanol and whereto said collected Raman scattered radiation from the sample is measured in the range of from about 2995–2860 and/or 1473–800 nm.

5. A process according to claim 1 wherein said oxygenated hydrocarbon comprises 1-butanol and wherein said collected Raman scattered radiation from the sample is measured in the range of from about 2961–2859 and/or 1475–382 nm.

6. A process according to claim 1 whereto said oxygenated hydrocarbon comprises 2-butanol and wherein said collected Raman scattered radiation from the sample is measured in the range of from about 2990–2861 and/or 1477–481 nm.

7. A process according to claim 1 wherein said oxygenated hydrocarbon comprises isobutanol and wherein said collected Raman scattered radiation from the sample is measured in the range of from about 2995–2860 and/or 1473–800 nm.

8. A process according to claim 1 wherein said oxygenated hydrocarbon comprises tertiary butyl alcohol and wherein said collected Raman scattered radiation from the sample is measured in the range of from about 3000–2898 and/or 1470–320 nm.

9. A process according to 1 wherein said oxygenated hydrocarbon comprises tertiary amyl alcohol and wherein said collected Raman scattered radiation from the sample is measured in the range of from about 3000–2690 and/or 1470–320 nm.

10. A process according to claim 1 wherein said oxygenated hydrocarbon comprises methyl tertiary butyl ether (MTBE) and wherein said collected Raman scattered radiation from the sample is measured in the range of from about 3011–2791 and/or 892–466 nm.

11. A process according to claim 1 wherein said oxygenated hydrocarbon comprises ethyl tertiary butyl ether (ETBE) and wherein said collected Raman scattered radiation from the sample is measured in the range of from about 3011–2791 and/or 892–466 nm.

12. A process according to claim 1 wherein said oxygenated hydrocarbon comprises tertiary amyl methyl ether (TAME) and wherein said collected Raman scattered radiation from the sample is measured in the range of from about 3011–2791 and/or 892–466 nm.

13. A process according to claim 1 wherein said oxygenated hydrocarbon comprises diisopropyl ether (DIPE) and wherein said collected Raman scattered radiation from the sample is measured in the range of frown about 2995–2860 and/or 1473–800 nm.

14. A process comprising:
   a) irradiating a sample of a liquid mixture comprising as oxygenated component methanol, 1-propanol, 2-propanol, 1-butanol, 2-butanol, isobutanol, tertiary butanol, tertiary amyl alcohol, methyl tertiary butyl ether (MTBE), ethyl tertiary butyl ether (ETBE), tertiary amyl methyl ether (TAME), and/or diisopropyl ether (DIPE) to produce Raman scattered radiation emitted from the sample;
   b) collecting Raman scattered radiation emitted from the sample;
   c) dispersing or transforming the collected Raman scattered radiation from the sample into spectra with intensities corresponding to the concentration of said components;

d) processing said spectra according to a regression model derived by multivariate analysis of Raman spectra, or derived from a mathematical function of Raman spectra, of liquid mixtures containing known concentrations of oxygenated hydrocarbons, to produce a control signal representative of the concentration of the oxygenated component in said mixture;

e) controlling a process in response to said control signal.

15. The process of claim 14 wherein the liquid mixture is a hydrocarbon mixture.

16. The process of claim 14 wherein the sample is irradiated with near infrared radiation.

17. The process of claim 14 wherein the sample comprises methanol.

18. The process of claim 14 wherein the sample comprises 1-propanol.

19. The process of claim 14 wherein the sample comprises 2-propanol.

20. The process of claim 14 wherein the sample comprises 1-butanol.

21. The process of claim 14 wherein the sample comprises 2-butanol.

22. The process of claim 14 wherein the sample comprises isobutanol.

23. The process of claim 14 wherein the sample comprises tertiary butyl alcohol.

24. The process of claim 14 wherein the sample comprises tertiary amyl alcohol.

25. The process of claim 14 wherein said mixture comprises an alcohol.

26. A process according to claim 25 for determining the concentration of one or more alcohols or ethers in a liquid sample consisting essentially of hydrocarbons and said alcohols and/or said ethers, said process comprising:

a) irradiating the liquid sample with radiation from a near infrared source to produce Raman scattered radiation emitted from said sample;

b) collecting Raman scattered radiation emitted from the sample;

c) transferring collected Raman scattered radiation and dispersing or transforming the collected Raman scattered radiation from the sample into spectra with intensities corresponding to the chemical composition of the components of said sample and concentrations of said components;

d) processing said spectra according to a regression model derived by multivariate analysis of Raman spectra, or derived from a mathematical function of Raman spectra, of liquid mixtures containing known concentrations of alcohols and ethers, wherein the near infrared radiation source wavelength irradiating said sample is the same as, or correlated to, that employed in establishing said regression model;

e) determining the concentration of at least one alcohol or ether present by processing the spectral intensities according to said model and producing a control signal representative of the concentration of an alcohol and/or ether in said mixture.

27. A process according to claim 26 wherein said determining of the concentration comprises emitting a signal indicative of said concentration and wherein said signal is transmitted to a means for controlling a process for producing a product comprising said alcohol or said ether.

28. A process according to claim 26 wherein the intensities corresponding to the chemical composition of components are determined at wave numbers comprising 3300–2250 and/or 1900–175 $cm^{-1}$.

29. The process of claim 14 wherein said mixture comprises an ether.

30. A process according to claim 14 wherein said multivariate analysis is accomplished by mathematical manipulation comprising neural network partial least squares (PLS), principal component regression (PCR), and/or multiple linear regression (MLR).

31. A process according to claim 14 wherein said regression model is derived by methods comprising Raman intensity differences and/or spectral subtraction.

32. A process according to claim 14 wherein said mixture comprises a synthetic fuel mixture.

33. A process according to claim 14 wherein said control signal is used in a feed-forward or a feed-back control apparatus.

34. A process according to claim 14 wherein said Raman scattered radiation is collected from regions comprising the fingerprint (FP) region or the CH stretching region.

35. A process according to claim 14 wherein transforming said collected Raman scattered radiation is by FT Raman.

36. A process comprising:

a) irradiating a sample of a liquid mixture comprising hydrocarbons and further comprising as oxygenated hydrocarbon methanol, ethanol, 1-propanol, 2-propanol, 1-butanol, 2-butanol, isobutanol, tertiary butanol, tertiary amyl alcohol, methyl tertiary butyl ether (MTBE), ethyl tertiary butyl ether (ETBE), tertiary amyl methyl ether (TAME), and/or diisopropyl ether (DIPE) with near infrared radiation, producing Raman scattered radiation emitted from the sample;

b) collecting Raman scattered radiation emitted from the sample;

c) dispersing or transforming the collected Raman scattered radiation from the sample into spectra with intensities corresponding to the chemical composition of the components of the mixture of said sample and concentration of said components;

d) processing said spectra according to a regression model derived by multivariate analysis of Raman spectra, or derived from a mathematical function of Raman spectra, of liquid mixtures containing known concentrations of oxygenated hydrocarbons, to produce a control signal representative of the concentration of oxygenated hydrocarbon in said mixture;

e) controlling a process in response to said control signal.

37. The process of claim 36 wherein the liquid mixture is a hydrocarbon mixture.

38. An apparatus for the control of a process comprising in combination:

a) irradiating means for irradiating a sample of a liquid mixture comprising at least one oxygenated hydrocarbon to produce scattered radiation emitted from the sample;

b) Raman scattered radiation collecting means for collecting said Raman scattered radiation;

c) mathematical manipulation means for dispersing or transforming the collected Raman scattered radiation into spectra with intensities corresponding to the concentration of components of the mixture;

d) processing means liar processing said spectra according to a regression model derived by multivariate analysis of Raman spectra or mathematical function thereof, of liquid mixtures containing known concentrations of oxygenated hydrocarbons;

e) control signal generation means for producing a control signal representative of the concentration in said mixture of one or more of said oxygenated hydrocarbons;

f) control means responsive to said signal for controlling a process in response to said signal.

39. An apparatus according to claim 38 wherein said control means comprises means for controlling the quantity of at least one component being delivered to a blending zone in which fuels are blended to produce a finished fuel blend having a preset desired concentration of at least one oxygenated hydrocarbon.

* * * * *